(12) United States Patent
Buchalter

(10) Patent No.: US 8,231,533 B2
(45) Date of Patent: Jul. 31, 2012

(54) ULTRASOUND COUPLING DEVICE

(76) Inventor: Neal Buchalter, Short Hills, NJ (US)

( * ) Notice: Subject to any disclaimer, the term of this patent is extended or adjusted under 35 U.S.C. 154(b) by 1068 days.

(21) Appl. No.: 11/675,977

(22) Filed: Feb. 16, 2007

(65) Prior Publication Data

US 2008/0200810 A1 Aug. 21, 2008

(51) Int. Cl.
*A61B 8/14* (2006.01)
*A61B 8/00* (2006.01)
*A61H 1/00* (2006.01)

(52) U.S. Cl. ........ 600/459; 600/437; 600/439; 600/443; 601/2; 601/3; 601/4

(58) Field of Classification Search .......... None
See application file for complete search history.

(56) References Cited

U.S. PATENT DOCUMENTS

| | | | | |
|---|---|---|---|---|
| 4,051,842 A * | 10/1977 | Hazel et al. | ................... | 600/391 |
| 5,168,876 A * | 12/1992 | Quedens et al. | .............. | 600/376 |
| 5,394,877 A * | 3/1995 | Orr et al. | ........................ | 600/459 |
| 5,458,140 A | 10/1995 | Eppstein et al. | | |
| 5,522,878 A * | 6/1996 | Montecalvo et al. | ......... | 600/459 |
| 5,655,539 A | 8/1997 | Wang et al. | | |
| 5,656,015 A * | 8/1997 | Young | ............................... | 601/2 |
| 5,727,550 A * | 3/1998 | Montecalvo | ................... | 600/386 |
| 5,782,767 A * | 7/1998 | Pretlow, III | .................... | 600/443 |
| 6,719,699 B2 * | 4/2004 | Smith | ........................... | 600/459 |
| 2002/0049395 A1 | 4/2002 | Thompson et al. | | |
| 2002/0068871 A1 * | 6/2002 | Mendlein et al. | ............. | 600/459 |
| 2003/0149359 A1 * | 8/2003 | Smith | ........................... | 600/437 |
| 2003/0195420 A1 * | 10/2003 | Mendlein et al. | ............. | 600/437 |
| 2004/0064051 A1 | 4/2004 | Talish et al. | | |
| 2005/0090725 A1 | 4/2005 | Page et al. | | |
| 2005/0154313 A1 * | 7/2005 | Desilets et al. | ............... | 600/459 |
| 2005/0215901 A1 | 9/2005 | Anderson et al. | | |
| 2006/0163111 A1 * | 7/2006 | Baril | ............................. | 206/569 |
| 2006/0264751 A1 * | 11/2006 | Wendelken et al. | .......... | 600/439 |
| 2007/0185426 A1 * | 8/2007 | Ambrosio et al. | .............. | 602/43 |
| 2007/0239078 A1 * | 10/2007 | Jaeb | ................................. | 601/2 |
| 2008/0064961 A1 * | 3/2008 | Desilets et al. | ............... | 600/459 |

FOREIGN PATENT DOCUMENTS

EP 0800788 A1 10/1997

OTHER PUBLICATIONS

European Search Report for EP application No. 07009102.0 mailed Nov. 13, 2007.

* cited by examiner

*Primary Examiner* — Long V. Le
*Assistant Examiner* — Angela M Hoffa
(74) *Attorney, Agent, or Firm* — Hahn Loeser & Parks LLP

(57) ABSTRACT

An ultrasound coupling device for transmitting ultrasound waves from an ultrasound transducer to a test specimen, especially to a human or animal body, the coupling device having (a) a gel pad (2) for transmitting the ultrasound waves, (b) a support (3) having i) a transducer side (T), ii) a body side (B), and iii) an aperture (11) through the transducer side and the body side of the support (3), (c) the support (3) being provided with an adhesive element (13) on the body side, and (d) the gel pad (2) being received within the aperture (11) such that the gel pad (2) is adapted to contact the human or animal body when the body side of the support contacts the human or animal body.

17 Claims, 5 Drawing Sheets

ULTRASOUND COUPLING DEVICE

BACKGROUND OF THE INVENTION

1. Field of the Invention

The invention relates to an ultrasound coupling device for transmitting ultrasound waves from an ultrasound transducer to a human or animal body.

2. Background

Ultrasound is used in a variety of medical treatment methods. Especially, ultrasound is used to promote the healing of soft tissue injuries. Ultrasound is also used for monitoring a human or animal body, for example, for monitoring the velocity of a blood stream or the position of veins or arteries. Ultrasound is used for imaging the internal organs and systems of the body and for diagnosing abnormalities.

It is known, for example from US 2002/0049395 A1, to apply ultrasound to the thoracic cavity for cardiac rehabilitation over an extended treatment period. From U.S. Pat. No. 5,458,140 it is also known that the application of ultrasound can enhance transdermal drug delivery. Both applications require fixing a transducer head to the body for a long time.

Ultrasound waves are produced with an ultrasound transducer head and transmitted to the human or animal body via an ultrasound couplant. The ultrasound couplant reduces reflection of the ultrasound waves and thus increases the amount of ultrasound wave energy that is coupled into the body.

To enhance the focusing of an ultrasound transducer head, gel pads are used as couplants that are made of acoustically inert material. In particular, gel pads are used in cases when an ultrasound beam needs to be focused close to the surface of the skin.

For long term therapy existing devices may use a strap or other fiction device to fix the ultrasound transducer head and the gel pad to the human or animal body. It is a disadvantage that these methods/devices may hamper blood circulation. Additionally, many patients regard these kinds of methods/devices as uncomfortable.

Thus, the invention relates to the problem of mitigating disadvantages in known ultrasound coupling devices.

SUMMARY OF THE INVENTION

One object of the invention is to develop an ultrasound coupling device which has a simple structure and is easy and inexpensive to manufacture. For long term applications the ultrasound coupling device must to be removed frequently, for example to allow the patient to take a shower. Therefore, it is desirable to provide an inexpensive ultrasound coupling device that can be used as a disposable product.

The inventive coupling device can be adhered to a patient's body, where the patient may be an animal or a human being, so that no bandage or strap is needed. Additionally, the ultrasound device may be worn for a long time and in a comfortable way.

The adhesive element holds the ultrasound coupling device in place and enables a tight fit to the patient's skin. The gel pad is designed to fit inside the cavity of the transducer in order to provide sufficient contact.

Yet another object of the invention is to provide more comfort for patients. As the ultrasound coupling device is flat it can be worn under the clothes so that it is invisible to other persons. Further, the ultrasound coupling device has a low weight, which contributes to the wearing comfort. Due its simple construction, the ultrasound coupling device according to the invention can be manufactured as a throwaway product and can be changed regularly. This leads to an increased comfort for the patient.

In accomplishing the foregoing objects, there has been provided, according to the present invention, an ultrasound coupling device for transmitting ultrasound waves from an ultrasound transducer for a test specimen such as a human or animal body, said coupling device comprising a gel pad for transmitting said ultrasound waves that further comprises a support having a transducer side, a body side and a aperture to said transducer side and said body side, said support being provided with an adhesive element on said body side, and said gel pad being received within said aperture such that gel pad contacts said human or animal body if said body side of said support contacts said human or animal body.

In particular, a gel pad is a dimensionally stable body that contains or consists of a gel. The gel acts as a couplant, i.e. as a material that facilitates the transmission of ultrasonic energy from the transducer into the test specimen, especially into the human or animal body. Preferably, the gel pad is made from a gel that does not dry out when it is in contact with ambient air. Additionally, the gel is preferably not hygroscopic so that its consistency does not change during application. The gel may include a content of salts which is approximately equivalent to the content of salts in the human or animal skin so that no osmosis takes place when the gel pad is brought into contact with the skin.

The support may be any element that provides a stable connection between the skin of the human or animal body and the gel pad when the ultrasound coupling device is adhered to the human or animal body. The support may be made from plastics, rubber, latex, a woven textile, and a non-woven and may comprise reinforcing elements.

The adhesive element may have any shape. However, it is preferred that the adhesive element covers the entire or almost the entire body side of the support. This yields a strong and tight fit of the support to the skin of the human or animal body. It is preferred, but not necessary, that the adhesive element is homogeneous all over the body side of the support. It is possible that the support is provided with a plurality of adhesive elements, for example in form of concentric rings or polygons that encircle the aperture.

The gel pad has an edge and is encircled by a frame along this edge. This frame isolates the gel pad from ambient air and dirt. Further, this frame prevents liquid from the gel pad from leaking out and thus protects clothes of the patient from being contaminated with gel.

The frame is made of a foam. Foam is elastic, easy, lightweight, easy to manufacture, and waterproof. Further, the foam can be used to soak in an adhesive in case this is needed. In a preferred embodiment this foam is a reticulated foam. The reticulated foam becomes integrated into the gel pad due to the pores inherent in the foam and thus provides a safe hold of the gel pad. The edges of the foam are adhered to the support so that the foam is securely fixed to the support. That way, the reticulated foam enables the attachment of the gel pad to the skin adhesive.

The adhesive element may be capable of securely fixing the ultrasound coupling device to the human or animal body. The adhesive element may be such that it does not irritate the skin and provides for a sufficient adhesive force to couple the ultrasound transducer to a human or animal body for more than one day.

Preferably, said support comprises a liner covering said adhesive element. The liner protects the adhesive element against dirt, grease, and humidity and thus preserves it against loss of adhesive force during storage.

It is preferred that the adhesive element is a pressure-sensitive film. Pressure-sensitive films combine strong adhesion to little weight and small thickness.

In a preferred embodiment, the support is a flat patch. A flat patch is flexible and fits to uneven or curved parts of the human or animal body such as legs, arms, and so on.

Preferably, the flat patch has a width, a length, and a height, wherein the width or the length are at least ten times larger than the height. The width preferably exceeds six centimeters and the height is less than four millimeters.

It is preferred that the support comprises a fixing area on the transducer side that comprises a fastener which surrounds the aperture for fixing the ultrasound transducer. This fixing area preferably completely surrounds the aperture. This yields an especially strong connection between the ultrasound coupling device and the ultrasound transducer.

The fastener is preferably an adhesive that is located in cells of foam, especially in cells of the frame that surrounds the gel pad. This yields a simple construction which is easy to handle and to manufacture. Additionally, the support may include an additional strip of adhesive to further secure the transducer cable.

To provide for a save hold of the ultrasound coupling device on the human or animal body, the aperture is located close to a center of the support.

BRIEF DESCRIPTION OF THE DRAWINGS

The foregoing and other objects, aspect and advantages will be better understood from the following detailed description of a preferred embodiment of the invention with reference to the drawings, in which:

FIG. 4 is a perspective view of the transducer side as shown in FIG. 3 with a liner covering a fixing area for an ultrasound transducer being partly peeled of.

DETAILED DESCRIPTION OF THE DRAWINGS

Figure 1:
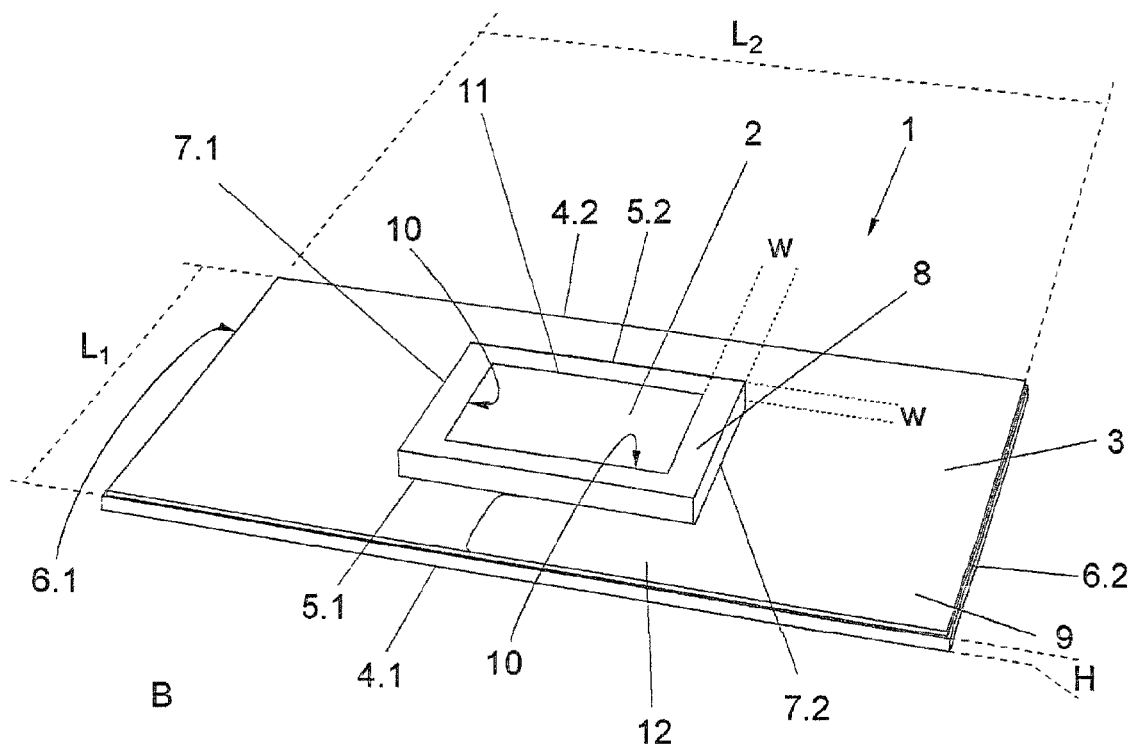
FIG. 1 is a perspective view on the body side of an ultrasound coupling device according to the invention.

Referring now to the drawings, and more particularly to FIG. 1, there is shown a body side B of an ultrasound coupling device 1 comprising a gel pad 2 and a support 3. Gel pad 2 has a substantially rectangular cross-section and consists of a isotonic gel. As the gel is isotonic, it can be brought into contact with a skin of human or animal body without losing water to the skin or drawing water from the skin.

Support 3 may have substantially rectangular shape and a height H. Gel pad 2 is located in the center of support 3. Long sides 4.1, 4.2 of support 3 are aligned with long sides 5.1, 5.2, respectively, of the gel pad 2. Accordingly, broadsides 6.1, 6.2 of the support 3 are aligned with broadsides 7.1, 7.2 of gel pad 2. Broadsides 6.1, 6.2 have a width $L_1$ and long sides 5.1, 5.2 have a length $L_2$.

Support 3 comprises a one-piece frame 8 which is made of a reticulated foam or generally of a open-celled foam. Frame 8 has a constant width w, and is irremovably fixed to a main body 9 of support 3, e.g. by a permanent adhesive. In an alternative embodiment, frame 8 has a circumferential groove that is received in a tongue-and-groove-like manner in main body 9.

Frame 8 has an inner edge 10 that surrounds an aperture 11 of support 3. The gel pad 2 is received within the aperture 11 (so that gel pad 2 is completely surrounded by inner edge 10 of frame 8) and is thus fixed to support 3.

Gel pad 2 is flush with frame 8 and both protrude from main body 9. If support 3 is brought into contact with the human body, gel pad 2 and frame 8 come into close contact with the human body as well.

Figure 2:
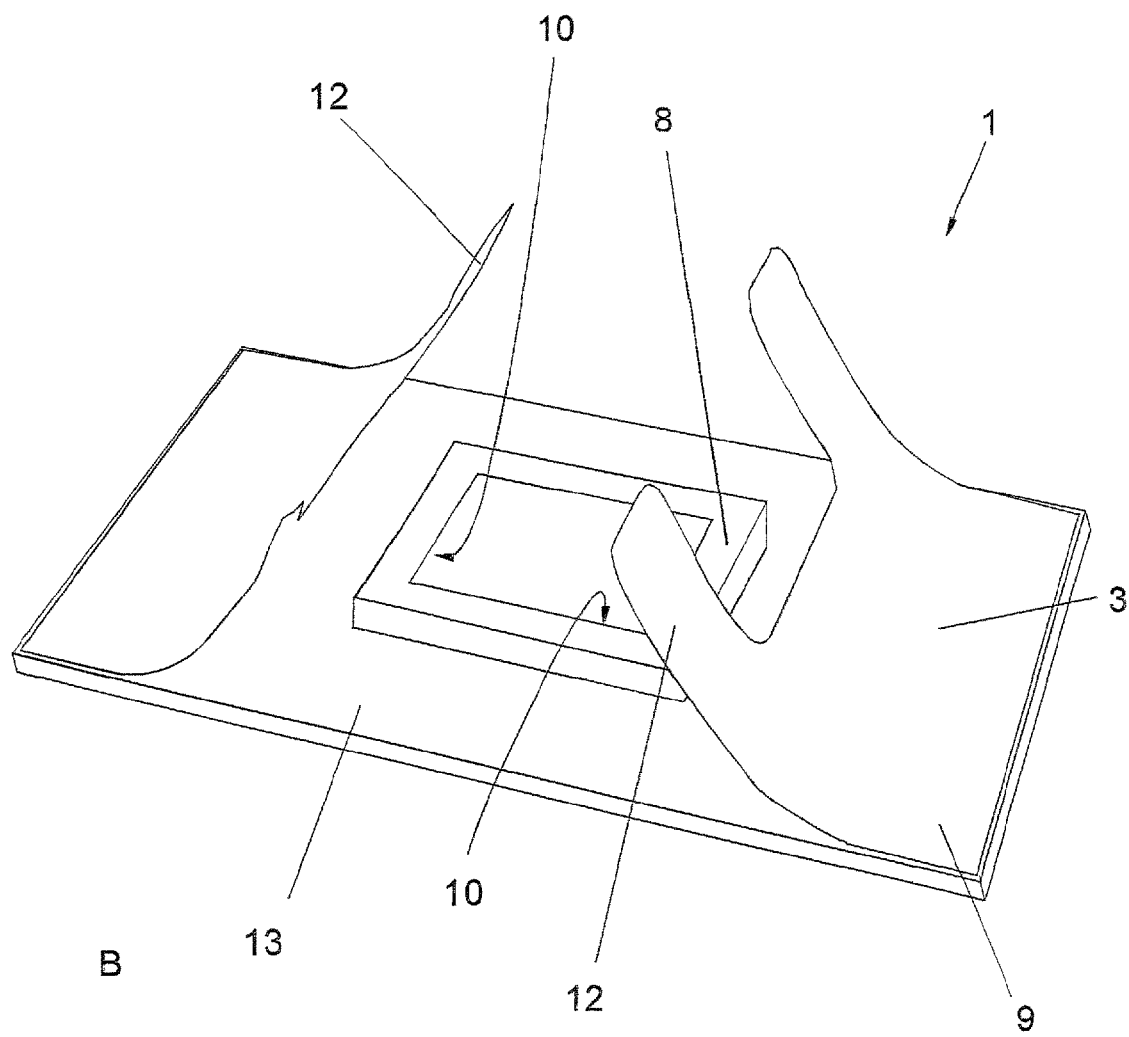
FIG. 2 is a perspective view on the coupling device of FIG. 1 with two parts of a liner partly peeled off.

Referring now to FIG. 2, it can be seen that main body 9 comprises a liner 12 covering an adhesive element in form of a pressure-sensitive film 13. Liner 12 covers the entire surface of pressure sensitive film 13 and can be peeled off to expose the adhesive surface. In the embodiment of FIG. 1, liner 12 does not cover gel pad 2 or frame 8. In an alternative embodiment, liner 12 may also cover those components.

Figure 3:
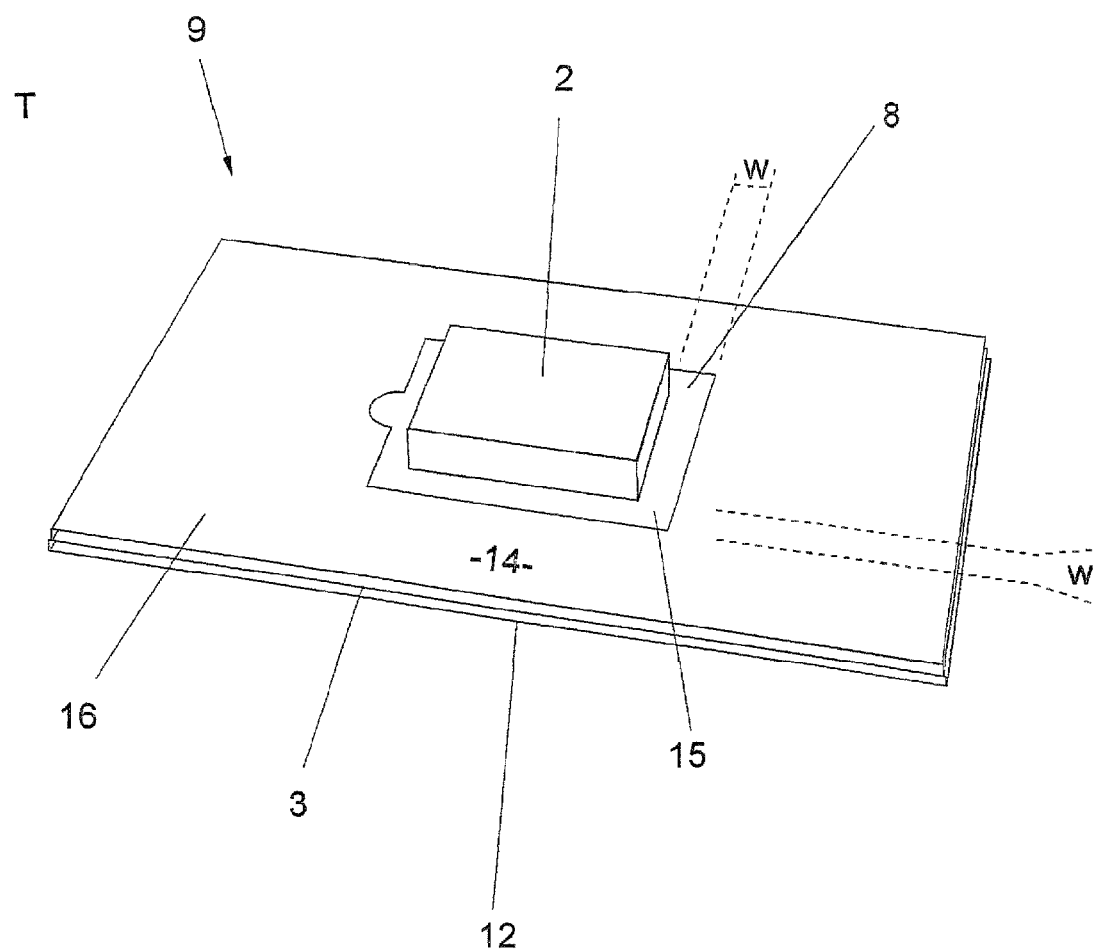
FIG. 3 is a perspective view on a transducer side of the ultrasound coupling device of FIGS. 1 and 2.

FIG. 3 shows a transducer side T of support 3. Gel pad 2 protrudes from a main body surface 14 of a flat foam pad 16. Foam pad 16 has the same shape as pressure-sensitive film 13 to which it is fixed. On the transducer side T, frame 8 is covered by a frame liner 15 which can be peeled off.

Alternate embodiment additional adhesive strips can be positioned on the surface to further secure the transducer or cable/wire. Further alternative additional linder can be positioned on the surface to expose additional adhesive to secure transducer or wire/cable.

Figure 4:
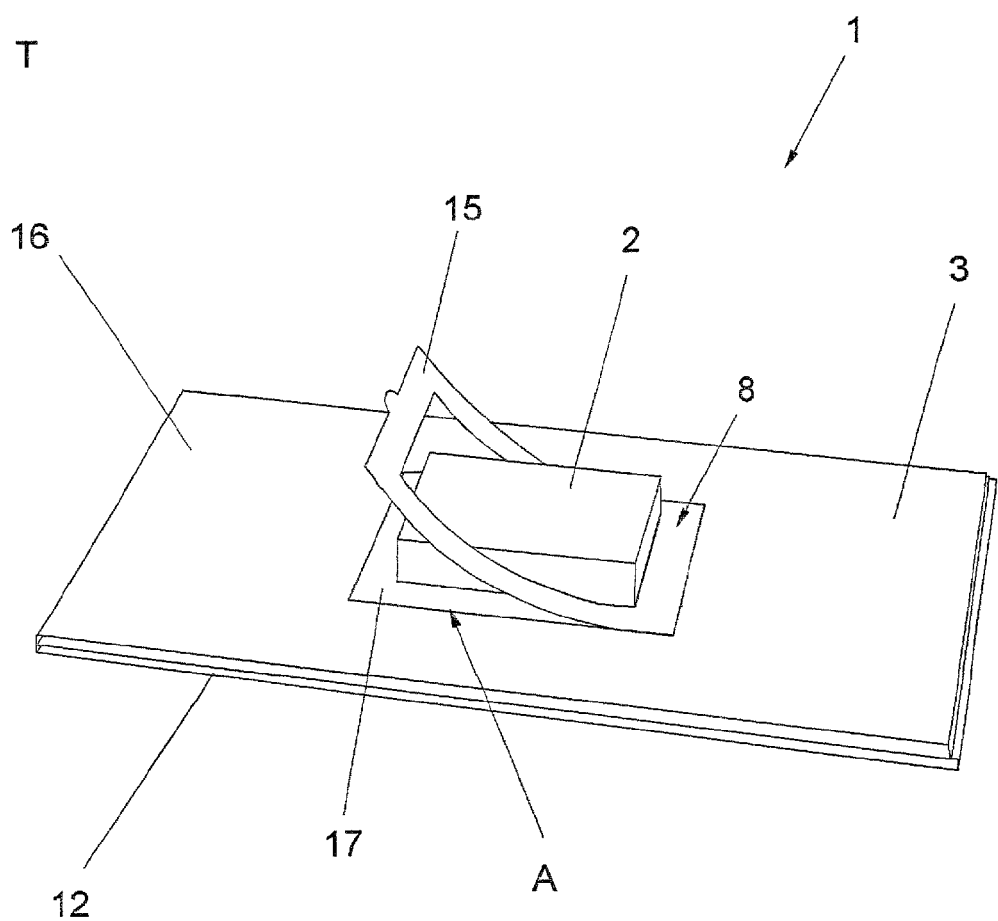

As can be seen in FIG. 4, the transducer side part of the frame 8 acts as a fixing area A for a transducer head (not shown). To fix the transducer head to the support 3, frame liner 15 is peeled off so that an adhesive 17 is exposed. The transducer head comprises a flange that may be fixed to fixing area A by the adhesive 17. The shape and size of the pad is determined by the design of the transducer. The transducer can be virtually any shape.

Figure 5A:
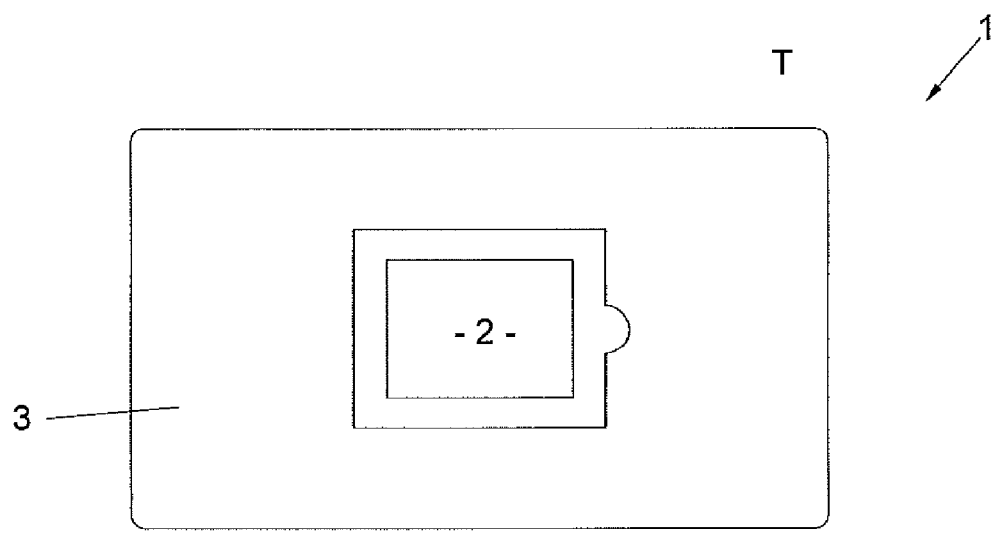
FIGS. 5a, 5b and 5c are schematic views of the ultrasound coupling device according to FIGS. 1 to 4.
Figure 5B:
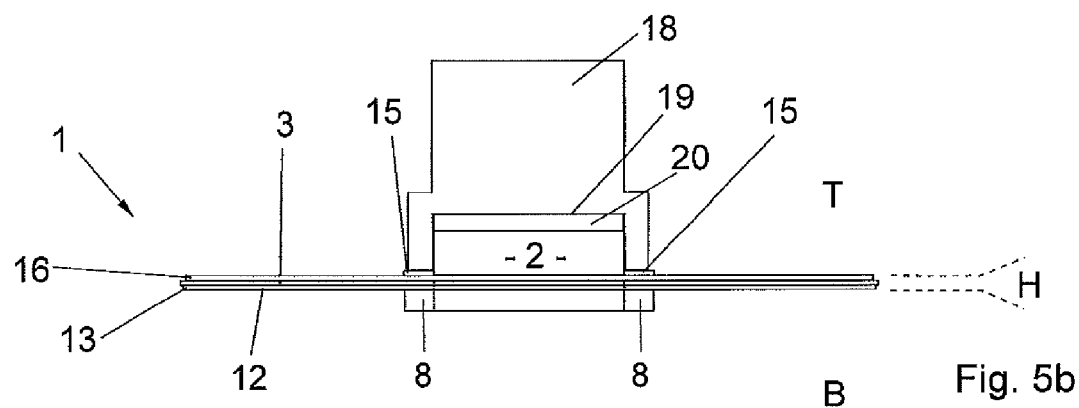
Figure 5C:
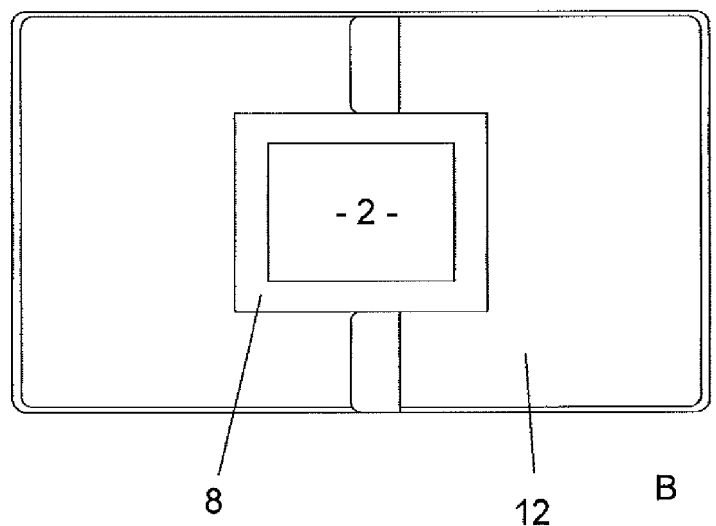

FIGS. 5a, 5b and 5c are to scale and show the ultrasound coupling device 1 of FIGS. 1 to 4. FIG. 5a shows transducer side T, FIG. 5b shows a sectional view, and FIG. 5c shows body side B.

An ultrasound device may be provided for transmitting ultrasound waves from an ultrasound transducer to a human or animal body. The ultrasound device may comprise an ultrasound coupling device (1) comprising a gel pad (2) for transmitting said ultrasound waves, a support (3) having a transducer side (T), a body side (B), and an aperture (11) through said transducer side and said body side of said support (3), said support (3) being provided with an adhesive element (13) on said body side, and said gel pad (2) being received within said aperture (11) such that said gel pad (2) contacts said human or animal body when said body side of said support contacts said human or animal body; and an ultrasound transducer (18), said ultrasound transducer (18) comprising a cavity (19) with an ultrasound transducer head (20), said cavity (19) having a sectional area, wherein said gel pad (2) is substantially shaped like said sectional area.

The ultrasound device may be provided in a method for monitoring a human or animal body. The method for monitoring a human or animal body may comprise the steps of providing the ultrasound device, attaching the ultrasound device to said human or animal body, powering said ultrasound transducer to generate ultrasound waves, receiving reflected or scattered ultrasound waves, and calculating a graphical representation from said scattered ultrasound waves.

A method for treating a human or animal body may comprise the steps of providing the ultrasound device, attaching the ultrasound device to said human or animal body, and powering said ultrasound transducer to generate ultrasound waves to promote a healing process of said human or animal body tissue. The method may be used for treating and promoting healing of soft tissue.

While the invention has been described in terms of a single embodiment, those skilled in the art will recognize that the invention can be practiced with modification within the spirit and scope of the appended claims.

Having thus described my or any invention, what I claim as new and desire to secure by Letters Patent is as follows:

1. An ultrasound coupling device for transmitting ultrasound waves from an ultrasound transducer to a human or animal body, the coupling device comprising:
   (a) a gel pad (2) for transmitting the ultrasound waves, the gel pad (2) having an edge (10),
   (b) a support (3) comprising a material selected from the group consisting of plastic, rubber, latex, woven textile, and non-woven textile, and having
      (i) a main body (9),
      (ii) a transducer side (T),
      (iii) a body side (B), and
      (iv) an aperture (11) through the transducer side (T) and the body side (B) of support (3),
   (c) the main body (9) being provided with an adhesive element (13) on the body side (B), the adhesive element (13) being capable of securely fixing the ultrasound coupling device (1) to the human or animal body,
   (d) the gel pad (2) being received within the aperture (11) such that the gel pad (2) is adapted to contact the human or animal body, and
   (e) the gel pad (2) being encircled by a frame (8) alongside the edge (10), the frame (8) being fixed to the main body (9), the frame (8) comprising foam,
   (f) the gel pad (2) and frame (8 protruding from the body side (B) of the main body (9), the gel pad (2) being flush with the frame (8),
   (g) the frame (8) comprising a fixing area (A) on the transducer side (T), the fixing area (A) comprising a fastener (17) surrounding the aperture (11) for fixing the ultrasound transducer.

2. The ultrasound coupling device according to claim 1, said frame (10) being reticulated foam.

3. The ultrasound coupling device according to claim 1, said support (3) comprising a liner (12) covering said adhesive element (13).

4. The ultrasound coupling device according to claim 1, said adhesive element comprising a pressure-sensitive film (13).

5. The ultrasound coupling device according to claim 1, said support (3) comprising a flat patch.

6. The ultrasound coupling device according to claim 5, said support (3) having a width (L1), a length (L2), and a height (H), said width (L1) or said length (L2) being at least ten times larger than said height (H).

7. The ultrasound coupling device according to claim 1, said fixing area (15) completely surrounding said aperture (11).

8. The ultrasound coupling device according to claim 7, said fixing area (A) having a substantially constant width (w).

9. The ultrasound coupling device according to claim 7, said fastener comprising an adhesive (17) capable of adhesively fixing said ultrasound transducer.

10. The ultrasound coupling device according to claim 9, said adhesive (17) being located in cells of a foam.

11. The ultrasound coupling device according to claim 10, said adhesive (17) being located in cells of said frame (8).

12. The ultrasound coupling device according to claim 1, said aperture (11) being located close to a center of said support (3).

13. An ultrasound device for transmitting ultrasound waves to a human or animal body, said ultrasound device comprising:
   (a) an ultrasound coupling device (1) according to claim 1; and
   (b) an ultrasound transducer, said ultrasound transducer comprising a cavity with an ultrasound transducer head, said cavity having a sectional area, wherein said gel pad (2) is substantially shaped like said sectional area.

14. The ultrasound device according to claim 13,
   (a) said support comprising the fixing area (A) comprising the fastener (17) surrounding said aperture (11) for fixing said ultrasound transducer,
   (b) said ultrasound device comprising an ultrasound transducer head, said cavity having a sectional area,
   (c) said gel pad (2) being substantially shaped like said sectional area and
   (d) said fixing area (A) being attached to a flange of said ultrasound transducer.

15. A method for monitoring a human or animal body comprising the steps of:
   (a) providing an ultrasound device for transmitting ultrasound waves to a human or animal body, said ultrasound device comprising:
      (i) an ultrasound coupling device (1) comprising:
         a gel pad (2) capable of transmitting ultrasound waves, the gel pad (2) having an edge (10), and
         a support (3) comprising a material selected from the group consisting of plastic, rubber, latex, woven textile, and non-woven textile, and having a main body (9), a transducer side (T), a body side (B), and an aperture (11) through said transducer side and said body side of said support (3), said main body (9) being provided with an adhesive element (13) on said body side, the adhesive element (13) being capable of securely fixing the ultrasound coupling device (1) to the human or animal body, said gel pad (2) being received within said aperture (11) such that said gel pad (2) is adapted to contact said human or animal body when said body side of said support contacts said human or animal body; and the gel pad (2) being encircled by a frame (8) alongside the edge (10), the frame (8) being fixed to the main body (9), the frame (8) comprising foam, the gel pad (2) and frame (8) protruding from the body side (B) of the main body (9), the gel pad (2) being flush with the frame (8), and the frame (8) comprising a fixing area (A) on the transducer side (T), the fixing area (A) comprising a fastener (17) surrounding the aperture (11) for fixing the ultrasound transducer;
      (ii) an ultrasound transducer, said ultrasound transducer comprising a cavity with an ultrasound transducer head, said cavity having a sectional area, wherein said gel pad (2) is substantially shaped like said sectional area
   (b) fixing said ultrasound transducer on said fixing area (A) of said ultrasound coupling device (1) by said fastener (17) such that said gel pad (2) fits into said cavity of said ultrasound transducer,
   (c) attaching the ultrasound device to said human or animal body,
   (d) powering said ultrasound transducer to generate ultrasound waves, (e) receiving reflected or scattered ultrasound waves, and
(f) calculating a graphical representation from said reflected or scattered ultrasound waves.

16. A method for treating a human or animal body comprising the steps of:
   (a) providing an ultrasound device for transmitting ultrasound waves to a human or animal body, said ultrasound device comprising:
      (i) an ultrasound coupling device (1) comprising:
         a gel pad (2) capable of transmitting ultrasound waves, the gel pad (2) having an edge (10),
         a support (3) comprising a material selected from the group consisting of plastic, rubber, latex, woven textile, and non-woven textile, and having a main body (9), transducer side (T), a body side (B), and an aperture (11) through said transducer side and said body side of said support (3), said main body (9) being provided with an adhesive element (13) on said body side, the adhesive element (13) being capable of securely fixing the ultrasound coupling device (1) to the human or animal body,
         said gel pad (2) being received within said aperture (11) such that said gel pad (2) is adapted to contact said human or animal body when said body side of said support contacts said human or animal body; and the gel pad (2) being encircled by a frame (8) alongside the edge (10), the frame (8) being fixed to the main body (9), the frame (8) comprising foam, the gel pad (2) and frame (8) protruding from the body side (B) of the main body (9), the gel pad (2) being flush with the frame (8), and the frame (8) comprising a fixing area (A) on the transducer side (T), the fixing area (A) comprising a fastener (17) surrounding the aperture (11) for fixing the ultrasound transducer;
      (ii) an ultrasound transducer, said ultrasound transducer comprising a cavity with an ultrasound transducer head, said cavity having a sectional area, wherein said gel pad (2) is substantially shaped like said sectional area;
   (b) fixing said ultrasound transducer on said fixing area (A) of said ultrasound coupling device (1) by said fastener (17) such that said gel pad (2) fits into said cavity of said ultrasound transducer,
   (c) attaching the ultrasound device to said human or animal body, and
   (d) powering said ultrasound transducer to generate ultrasound waves to promote a healing process of said human or animal body tissue.

17. The method according to claim 16, wherein said gel pad (2) is adapted to contact said human or animal body tissue being soft tissue.

* * * * *

UNITED STATES PATENT AND TRADEMARK OFFICE
CERTIFICATE OF CORRECTION

PATENT NO.        : 8,231,533 B2
APPLICATION NO.   : 11/675977
DATED             : July 31, 2012
INVENTOR(S)       : Neal Buchalter It is certified that error appears in the above-identified patent and that said Letters Patent is hereby corrected as shown below:

In Claim 1: Column 5, line 35, "(8" should read --(8)--.
In Claim 9: Column 5, line 61, "claim 7" should read --claim 1--.

Signed and Sealed this
Second Day of October, 2012

David J. Kappos
*Director of the United States Patent and Trademark Office*